United States Patent [19]

Nishikawa et al.

[11] Patent Number: 4,599,739
[45] Date of Patent: Jul. 8, 1986

[54] DENTAL RADIOGRAPHIC APPARATUS FOR PHOTOGRAPHING ENTIRE JAWS

[75] Inventors: Kazuo Nishikawa; Keisuke Mori, both of Kyoto, Japan

[73] Assignee: Kabushiki Kaisha Morita Seisakusho, Kyoto, Japan

[21] Appl. No.: 692,830

[22] Filed: Jan. 18, 1985

[30] Foreign Application Priority Data

Jan. 20, 1984 [JP] Japan .................................. 59-9106

[51] Int. Cl.$^4$ .......................... A61B 6/14; G03B 42/02
[52] U.S. Cl. ........................................ 378/39; 378/40; 378/98
[58] Field of Search ........................ 378/38, 39, 40, 98

[56] References Cited

U.S. PATENT DOCUMENTS

| | | | |
|---|---|---|---|
| 3,737,660 | 6/1973 | Ando et al. ............................ | 378/39 |
| 4,039,837 | 8/1977 | Ohta et al. ............................ | 378/40 |
| 4,263,513 | 4/1981 | Palluet .................................. | 378/40 |

Primary Examiner—Alfred E. Smith
Assistant Examiner—T. N. Grigsby
Attorney, Agent, or Firm—Koda and Androlia

[57] ABSTRACT

A radiographic apparatus for photographing the entire jaws designed to make a tomogram of a curved plane approximate to a dental arch by the locus of center of rotation of the X-ray beam projected from an X-ray source onto an X-ray film holder describing an approximately V-shaped envelope which forms an apex on an approximate medial line and recedes from the apex toward the left and right of the approximate medial line by moving a rotary arm around a patient, the arm having the X-ray source at one end and the X-ray film holder at the other end thereof, wherein the apparatus comprises a means for changing straight-line distance on the approximate medial line between the apex and receding point of limit of the envelope and a means for indicating the distance of shift thus changed or a means for automatically moving the indication means a distance equal to the distance of shift.

6 Claims, 5 Drawing Figures

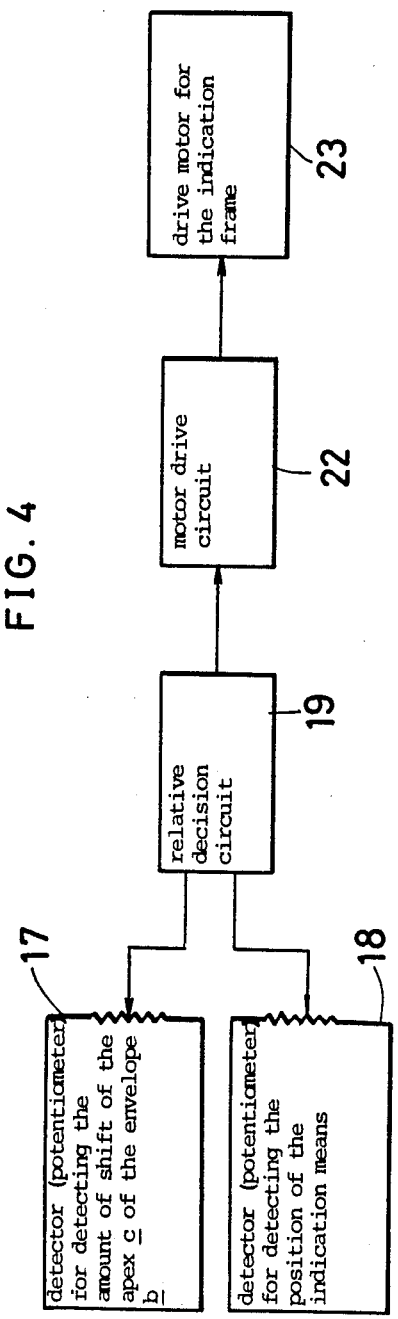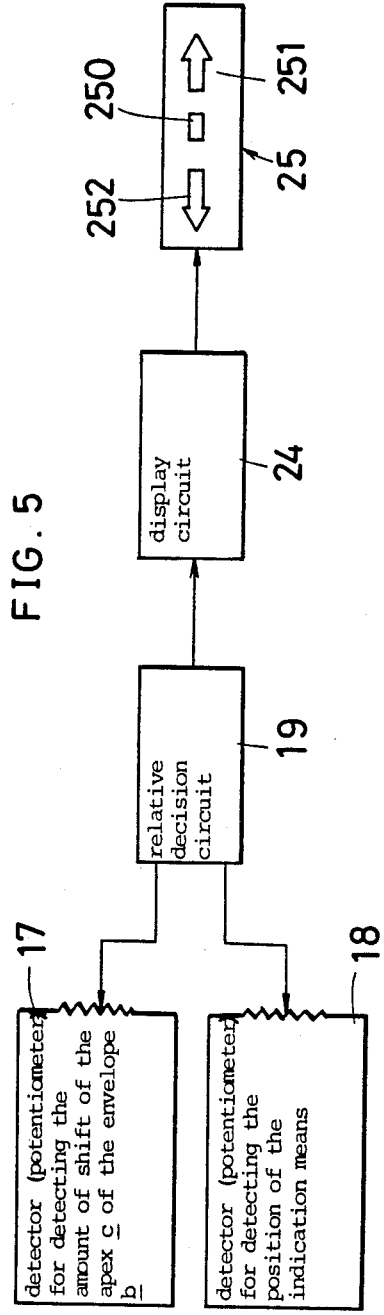

DENTAL RADIOGRAPHIC APPARATUS FOR PHOTOGRAPHING ENTIRE JAWS

BACKGROUND OF THE INVENTION

1. Field of the Invention

This invention relates to improvements in a dental radiographic apparatus for photographing the entire jaw.

2. Prior Art

The present inventor previously filed a patent application in the form of U.S. patent application Ser. No. 667,769 on Nov. 2, 1984 for a radiographic apparatus for photographing the entire jaws capable of irradiating X-rays substantially normally to any position of the dental arch in proportion to the individual differences in the dental arch of a patient and which is free from ghost images in the mandibular ramuses. This previous invention, in which a locus of rotation of X-ray beam describes a substantial V-shaped envelope receding from the apex formed on the approximate medial line to the left and right of the medial line, changes the straight-line distance on the approximate medial line between the apex and receding point of limit of the envelope and structurally comprises fixed rails secured to a fixed frame and an arm freely movable on the rails. The invention was designed to change the straight-line distance by moving the arm with respect to the fixed frame. When this straight-line distance changes, a sectional plane curve also follows the change, with the result that there is a case wherein a patient must be positioned in the thus changed position. The reason for this is explained with reference to FIG. 1 of the accompanying 1 drawings of this invention. In the figure, the character designates an approximate medial line, and a designates an approximate dental arch of a patient, namely a tomographic plane curve (curved plane), and b designates an envelope described by a locus of movement of center of rotation of X-ray beam, the envelope being approximately V-shaped by being curved in a manner to recede left and right from the apex c of the appropriate medial line b. (In the previous invention, the envelope is shown as being approximately triangular, instead of the approximate V-shape, but this is merely a difference in the manner of expression and both expressions are substantially the same in content.) Now, when the arm is moved from this state by a mechanism to be later described, the apex c of the envelope b is moved to $c_1$ and in proportion thereto, the envelope b is moved to $b_1$. Thereupon, an effective radius $r_1$ (a distance between an optional tangential line on the envelope and a curve a) extending from each position of the envelope b to the tomographic plane curve a also changes to $r_1$. Consequently, a locus $a_1$ of this effective radius $r_1$ provides a new tomographic plane curve. Namely, the initial tomographic plane curve a must be shifted to position $a_1$. For this reason, for example, according to a photographing method in which the front tooth region of a patient is brought into agreement with position $a_{10}$ on the tomographic plane curve $a_1$, it is impossible to make exact tomogram if this position $a_o$ is not shifted to the position $a_{10}$ on the tomographic plane curve $a_1$. In other words, when the apex c of the envelope is shifted to position $c_1$ along the approximate medial line l, the initial tomographic curve a must also be shifted to position $a_1$ in amounts corresponding to the straight-line distance of shift d thus made by shift of the apex c.

By the way, an attempt to change the envelope b in the manner described above was made for the first time by the present invention, and there has so far existed nothing or no means of indicating the aforestated amount of shift d in terms of a device.

SUMMARY OF THE INVENTION

Accordingly, this invention provides a means for mechanically or electrically indicating an amount of shift d in combination with an envelope variable type radiographic apparatus. The invention also provides in the form of further development a means for automatically shifting the indication means.

A detailed description will now be given of preferred embodiments of the invention with reference to the accompanying drawings.

BRIEF DESCRIPTION OF THE DRAWINGS

FIG. 4 is a circuit diagram of an all-automatic control type radiographic apparatus embodied in another form of the invention; and FIG. 5 is a circuit diagram of a light display manual control type radiographic apparatus embodied in still another form of the invention.

DETAILED DESCRIPTION OF THE INVENTION

Figure 1:
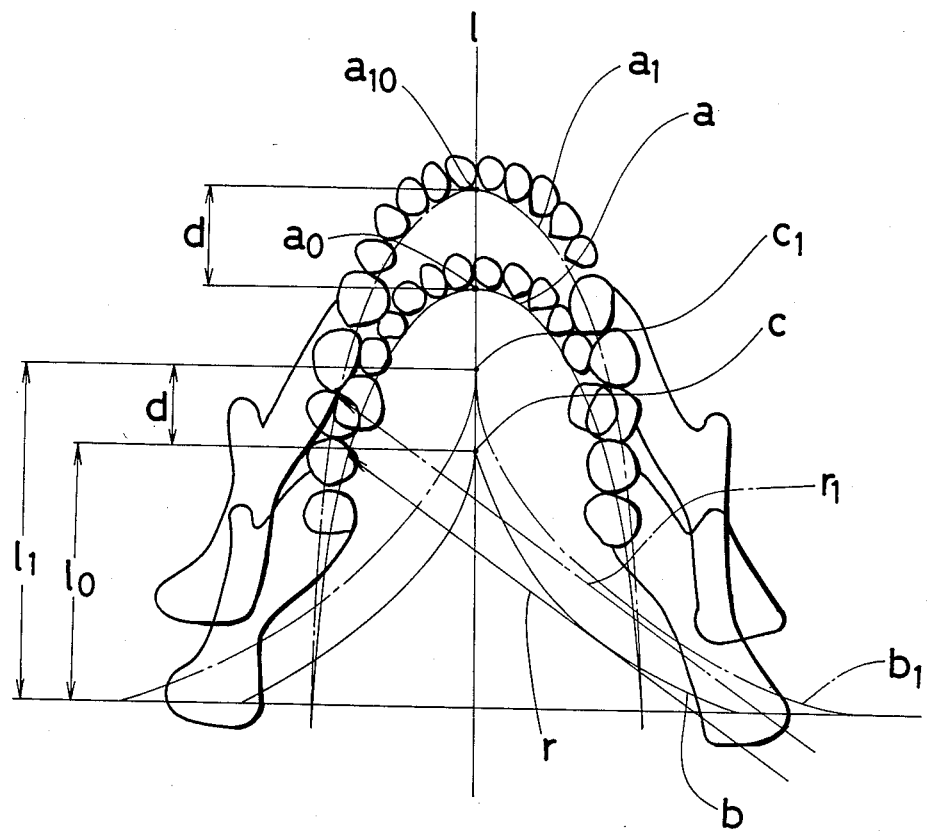
FIG. 1 is a view explaining the relation between the locus of shift of center of rotation of X-ray beam and a tomographic plane curve with reference to an approximate medial line.
Figure 2:
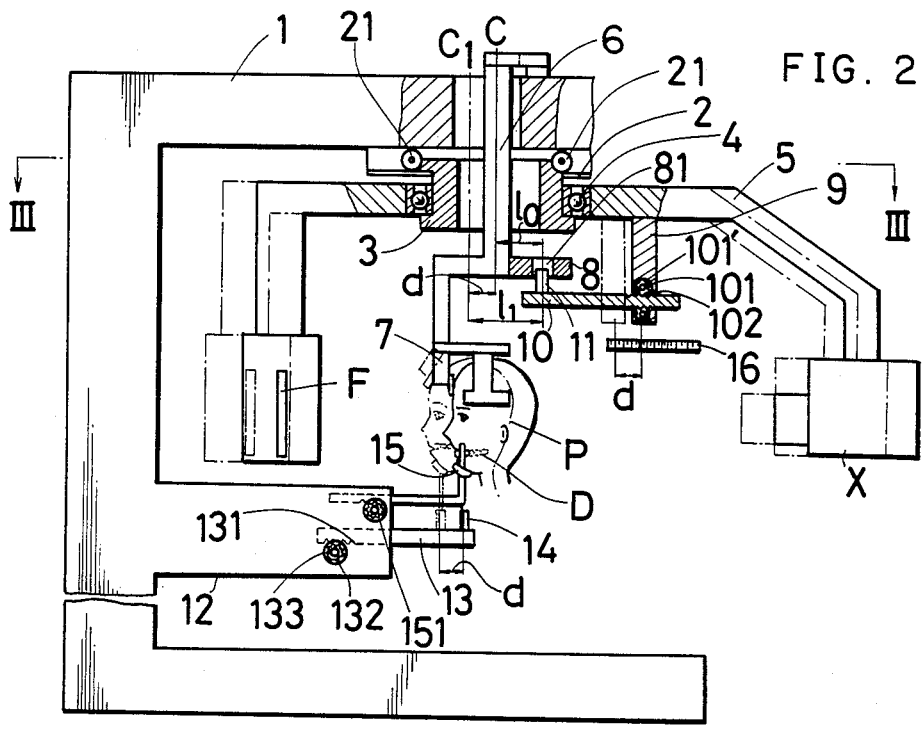
FIG. 2 is a longitudinal sectional side view showing, in part, an apparatus embodied in one form of the invention.
Figure 3:
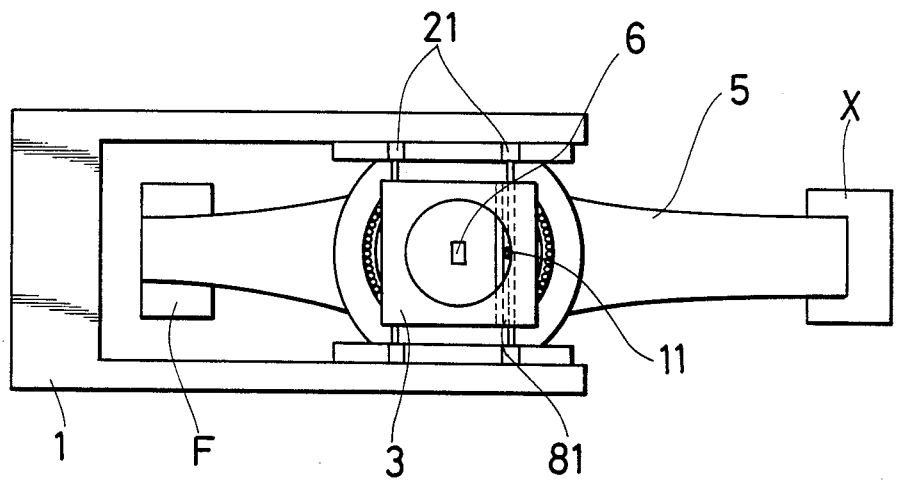
FIG. 3 is a sectional view taken along the line III—III of FIG. 2.

FIGS. 2 and 3 show an embodiment of a means for mechanically indicating an amount of shift d. A horizontally rotating arm 5 is rotatably fitted through a bearing 4 over a cylindrical holder 3 stradles by rollers 21, 21 on a rail 2 fixed to the underside of an upper frame of a floor type fixed frame 1 in parallel relation with respect to an approximate medial line. On one side of the arm 5 is disposed an X-ray source X and on the other side of the arm is disposed an X-ray film holder F in opposed relation to the X-ray source X. A suspension rod 6 is suspended passing through the frame 1 and the holder 3 and has a head fixing means means 7 at one end and a regulating member 8 at the other end thereof. A groove 81 normal to the rail 2 passes through the regulating member 8 and a suspension rod 9 is suspended from the arm 5. To the lower portion of the rod 9 is connected a horizontal rod 10 integrally with the suspension rod 9 in the manner that the rod 10 can freely be moved and stopped horizontally. A pin 11 at the end of the rod 10 is loosely fitted into the groove 81 in the manner that the pin 11 can be moved freely. The horizontal rod 10 is formed with a rack 102 and the suspension rod 9 is formed with a pinion 101 so that both rods 10 and 9 may mesh with each other. The pinion 101 is provided with a coaxial handle 101'. By operating the handle 101', the center of rotation of the rotary arm 5 is made movable and lockable. In the embodiment, the distance between the pin 11 and the pinion 101 is thus changed to vary the envelope b (to be later described in detail). Also, in the middle of the frame 1 a bracket 12 projects horizontally in parallel relation with respect to the approximate medial line. At the end of the bracket 12 are disposed a chin rest 15 and an indication means 13 which are independently controllable for moving in the direction of the medial line. From the end of the means 13 is projected upwardly for example a light beam 14 for indicating a tomographic plane position. By this beam 14 is indicated a position of front teeth or a cuspid (shown in the drawing as a cuspid) of the tooth row D of a patient P. The patient is caused to hold himself in the indicated position. In the structure described above, the arm 5 makes free rotation around the movable holder 3 and makes combined movements of the holder 3 in the direction of rails 2 and in the direction of the groove 81 normal to the rails 2 in accordance with driving and power transmission mechanism. By the rotation of the rotary arm 5 effected as above, the center of rotation of X-ray beam describes envelopes b in FIG. 1, while the X-ray source X and a film F move around the head of the patient P describing a locus of an appropriate dental arch. If the pinion 101 of the rod 9 is rotated with respect to the rack 102 formed in the horizontal rod 10, the whole of the arm 5 is shifted in the direction indicated by alternate long and short dash lines. Namely, the center of rotation of the rotary arm 5 is shifted from c to $c_1$ to change the distance between the pin 11 and the center of rotation from $l_o$ to $l_1$. This amount of shift d corresponds to the distance of apex c to $c_1$ in FIG. 1, and accordingly unless tomographic plane curve a at point $a_o$ is shifted to point $a_{10}$ by a distance corresponding to the amount of shift d, the tomographic plane of a cuspid (or front teeth) of the tooth row D of the patient P cannot be photographed.

Now, referring to the invention in conjunction with FIG. 1, the whole of rotary arm 5, namely the amount of shift d of center of rotation of the suspension rod 9 of rotary arm 5 is measured as by a scale 16 attached to the neighborhood of the suspension rod 9. On the other hand, the indication frame 13 is made free to move back and forth with respect to a bracket 12 as by a rack 131 and a pinion 132 and a knob 133 coaxially mounted to the pinion 132 so as to provide an indication means. If in this case the frame 13 is moved forwardly a distance corresponding to the distance d read by the scale 16 by operating the knob 133, a new position of a light beam 14 exactly indicates a new tomographic plane position relative to the tooth row D of the patient P. Accordingly, operating likewise the knob 151 in this position to regulate the chin rest 15, the patient P is caused to hold himself in position. When it is desired to reverse the direction of movement, it is only necessary to move back the indication frame 13 and chin rest 15 on entirely the same principles. In this connection, the head fixing means 7 is also moved by a mechanism not shown in amounts equivalent to the amount of shift of the frame 13 and the rest 15. When it is desired to measure the amount of advance and retreat of the indication means 13, the measurement is taken with ease by additionally attaching a scale not shown by beforehand measuring the distance of advance or retreat for each specified rotation of the knob 133. Furthermore, for detail of the structure and its function in FIGS. 2 and 3 refer to the prior art application aforementioned in the introductory description of the present invention.

FIG. 4 shows an embodiment of the invention including a means for electrically measuring the amount of shift and for automatically moving the indication means equivalent to the amount of shift. FIG. 5 shows another embodiment of the invention which is designed to electrically measure the amount of shift, indicate the proper position of the indication means by a light display means, and manually move the indication means in accordance with the display means.

In FIG. 4, the numeral 17 designates a detector (potentiometer) for detecting the amount of shift of the apex c of the envelope b, the detector being designed to catch the amount of shift by an electric signal, for example, to detect the rotation of the handle 101' as by a potentiometer. The numeral 18 designates a detector (potentiometer) for detecting the position of the indication means, the detector being designed to catch the position of the indication frame 13 by an electric signal. Position information obtained from both detectors 17 and 18 is inputted into a relative (comparative) decision circuit 19 to adjudge or not the indication frame 13 is in the position where the frame 13 should properly be corrected by shift of the apex c of the envelope or whether it should be corrected in the forward direction or in the backward direction and how large the amount of correction should be if the frame 13 is in the position in which it should be corrected. The output signal thus adjudged for the amount of correction is inputted into a motor drive circuit 22 to specify the direction of rotation of a drive motor 23 for the indication frame 13 (the motor 23 is for example a pulse motor for imparting positive and negative rotation to the aforestated pinion 132 and is not shown in FIG. 2 but is shown in FIG. 4) and gives a motor drive signal necessary for the amount of correction to the motor 23 to impart a necessary number of rotations to the motor to bring the light beam 14 of the indication frame 13 all-automatically into proper position. In this manner, the embodiment in FIG. 4 is designed to move the indication frame 13 by all-automatic operation instead of manual operation of the knob 133 in the embodiment in FIG. 2. The embodiment in FIG. 5 is designed to make the light display means adjudge whether or not the indication frame 13 is in proper position and in what direction and amount the frame 13 should be corrected if it is not in proper position. In this case, an output signal from the relative decision circuit 19 in FIG. 4 is inputted into a display circuit 24 to make an output signal from the circuit 24 operate a light display unit 25. For example, the display unit 25 selectively displays the position of the frame 13 by means of display lamps respectively in the form of a rightward arrow 251 when correction in the forward direction is necessary, a leftward arrow 252 when correction in the backward direction is necessary, and a neutral dot 250 between the two arrows when the frame 13 is in proper position. For example, the knob 133 is operated at lighting up of the leftward arrow 252 to move the light beam 14 leftwardly and to stop movement when the neutral dot 250 puts on a light. It is understood that various modifications may be made for this positioning of the frame 13 in such a manner that when the frame 13 has taken proper position, an OK signal is given instead of the neutral dot 250 putting on a light, or the display unit 25 itself puts out a light. The invention, in short, is applicable equally to all the structures designed to change positioning of a patient by changing an envelope.

As apparent from the description given above, the invention is significant in providing a clear tomographic picture in that the invention enables necessary shift of the tomographic position of a patient with great ease because it includes a means for indicating the amount of shift made by the apex along the approximate medial line when the envelope, i.e. the locus of center of rotation of X-ray beam changes in proportion to individual differences in the tooth row of the patient. Furthermore, the invention additionally provides the great advantage that when a means for all-automatically moving the indication means itself to a necessary position is employed, control and operation by an operator are rendered unnecessary.

Having described my invention as related to the embodiments shown in the accompanying drawings, it is my intention that the invention be not limited by any of the details of description, unless otherwise specified, but rather be construed broadly within its spirit and scope as set out in the appended claims.

We claim:

1. A radiographic apparatus for photographing the entire jaws designed to make a tomogram of a curved plane approximate to a dental arch by the locus of center of rotation of the X-ray beam projected from an X-ray source onto an X-ray film holder describing an approximately V-shaped envelope which forms an apex on an approximate medial line and recedes from the apex toward the left and right of the approximate medial line by moving a rotary arm around a patient without interference with the patient, the arm having the X-ray source at one end and the X-ray film holder at the other end thereof, said apparatus being characterized in that it comprises a means for changing straight-line distance on the approximate medial line between the apex and receding point of limit of the envelope and a means for indicating the distance of shift thus changed or a means for automatically moving the indication means a distance equal to the distance of shift.

2. An apparatus according to claim 1, wherein said straight-line distance changing means includes rails fixed to a fixed frame in parallel relation with the approximate medial line and a horizontal rotary arm movable in its center of rotation along the rails and wherein said indication means includes an indication frame attached to the front end of a bracket so as to be movable back and forth, the bracket projecting from the fixed frame parallelly to the approximate medial line.

3. An apparatus according to claim 2, further including a means for manually moving the indication frame a distance to the distance of shift of the horizontal arm along the rails.

4. An apparatus according to claim 1, wherein said means for automatically moving the indication means in parallel relation to the approximate medial line comprises a relative decision circuit, the circuit relatively deciding the respective pieces of electric position information from a means for detecting the amount of shift of the envelope and from a means for detecting the position of the indication means to thereby output the direction of shift and amount of shift due to the indication means in terms of a position signal, and a motor drive circuit which drives an indication means driving motor in the direction of shift and in the amount of shift in accordance with the position signal.

5. An apparatus according to claim 1, wherein the direction of shift and the amount of shift of the indication means are indicated by a light display means and the indication means is manually shifted in accordance with the light display means and wherein the light display means comprises a relative decision circuit, the circuit relatively deciding the respective pieces of electric position information from a potentiometer for detecting the amount of shift of the envelope and from a potentiometer for detecting the position of the indication means to thereby output the direction of shift and amount of shift due to the indication means in terms of a position signal, a display circuit which outputs to display the direction of shift and amount of shift in accordance with the output of the relative decision circuit, and a display unit which displays the direction of shift and amount of shift in accordance with the output of the display circuit.

6. An apparatus according to claim 5, wherein the direction of shift is displayed by a lit-up arrow and the amount of shift is displayed in the form of a lit-up dot while the amount is not in agreement with the proper amount of shift and when the amount is brought into agreement, the lit-up dot is put out.

* * * * *